United States Patent
Zhao et al.

(10) Patent No.: US 11,208,530 B2
(45) Date of Patent: *Dec. 28, 2021

(54) MULTI-ARM POLYETHYLENE GLYCOL, PREPARATION METHOD AND USES THEREOF

(76) Inventors: Xuan Zhao, Beijing (CN); Yuhe Zhao, Beijing (CN)

( * ) Notice: Subject to any disclaimer, the term of this patent is extended or adjusted under 35 U.S.C. 154(b) by 24 days.

This patent is subject to a terminal disclaimer.

(21) Appl. No.: 13/127,349

(22) PCT Filed: Sep. 28, 2009

(86) PCT No.: PCT/CN2009/001088
§ 371 (c)(1),
(2), (4) Date: Aug. 16, 2011

(87) PCT Pub. No.: WO2010/060260
PCT Pub. Date: Jun. 3, 2010

(65) Prior Publication Data
US 2011/0286956 A1 Nov. 24, 2011

(30) Foreign Application Priority Data
Nov. 3, 2008 (CN) .......................... 200810225650.0

(51) Int. Cl.
*C08G 65/26* (2006.01)
*C08G 65/332* (2006.01)
*C08G 65/333* (2006.01)
*C08G 65/337* (2006.01)
*C08G 65/334* (2006.01)
*A61K 47/60* (2017.01)

(52) U.S. Cl.
CPC .......... *C08G 65/2609* (2013.01); *A61K 47/60* (2017.08); *C08G 65/337* (2013.01); *C08G 65/3322* (2013.01); *C08G 65/3344* (2013.01); *C08G 65/33337* (2013.01); *C08G 65/33396* (2013.01); *C08G 2650/24* (2013.01); *C08L 2203/02* (2013.01)

(58) Field of Classification Search
CPC ................ A61K 47/60; C08G 65/2609; C08G 65/3322; C08G 65/33337; C08G 65/33396; C08G 65/3344; C08G 65/337; C08G 2650/24; C08L 2203/02
See application file for complete search history.

(56) References Cited

U.S. PATENT DOCUMENTS

| | | | | |
|---|---|---|---|---|
| 2,441,597 A | * | 5/1948 | Remensnyder | C07C 43/135 568/619 |
| 5,728,895 A | * | 3/1998 | Wiggins | C09D 7/43 568/601 |
| 2004/0096507 A1 | | 5/2004 | Kwang et al. | |
| 2004/0170595 A1 | | 9/2004 | Zhao | |
| 2007/0031371 A1 | * | 2/2007 | McManus | A61K 31/74 424/78.37 |
| 2008/0039547 A1 | * | 2/2008 | Khatri et al. | 523/115 |
| 2010/0086678 A1 | | 4/2010 | Arthur et al. | |
| 2010/0087667 A1 | | 4/2010 | Khatri | |

FOREIGN PATENT DOCUMENTS

| | | | | |
|---|---|---|---|---|
| CN | 1706865 A | | 12/2005 | |
| CN | 1995094 A | | 7/2007 | |
| FR | 2350333 | * | 12/1977 | ............. B01J 31/00 |
| WO | 2008019383 A2 | | 2/2008 | |
| WO | 2008066787 A2 | | 6/2008 | |

OTHER PUBLICATIONS

Izunobi et al, Polymer Molecular Weight Analysis by 1H NMR Spectroscopy, J. Chem. Educ. May 31, 2011, 88, 1098-1104.
Dameron C. Lee et al, "A single dose of doxorubicin-functionalized bow-tie dendrimer cures mice bearing C-26 colon carcinomas", PNAS, Nov. 7, 2006, vol. 103, No. 45, 16649-16654.
Malvern Instruments Limited, "Static Light Scattering Technologies for GPC/SEC Explained", © 2013 Malvern Instruments Limited, MRK1919-03.
Ralf Knischka et al, "Functional Poly (ethylene oxide) Multiarm Star Polymers: Core-First Synthesis Using Hyperbranched Polyglycerol Initiators", Macromolecules 2000, 33, 315-320, © 2000 American Chemical Society.
Daniel Taton et al, "Polymerization of Ethylene Oxide with a Calixarene-Based Precursor: Synthesis of Eight-Arm Poly(ethylene oxide) Stars by the Core-First Methodology", Journal of Polymer Science: Part A: Polymer Chemistry, vol. 41, 1669-1676 (2003), © 2003 Wiley Periodicals, Inc.

* cited by examiner

*Primary Examiner* — Matthew P Coughlin
*Assistant Examiner* — Thurman Wheeler
(74) *Attorney, Agent, or Firm* — Jun He Law Offices P.C.; James J. Zhu

(57) ABSTRACT

A novel multi-arm polyethylene glycol (PEG) (I) and preparation method thereof. Active derivatives (II) based on the multi-arm PEG. Gels formed of the active derivatives. Drug conjugates formed of the active derivatives and drug molecules and uses thereof in medical preparation. The multi-arm PEG is formed by polymerizing ethylene oxide with pentaerythritol oligomers as initiator, wherein PEG is the same or different and is a —(CH2CH2O)m-, the average value of m is an integer of 3-1000, l is an integer more than or equal to 2. An 8-arm PEG is preferred, wherein l is equal to 3. The active derivatives (II) comprise link groups X attached to PEG and active end groups F attached to X.

8 Claims, No Drawings

MULTI-ARM POLYETHYLENE GLYCOL, PREPARATION METHOD AND USES THEREOF

FIELD OF THE INVENTION

The present invention relates to a polyethylene glycol, especially a multi-arm polyethylene glycol, its active derivatives, preparation method thereof, the conjugation with pharmaceutical molecules and gel materials formed from the polyethylene glycol. The invention also relates to the use of the novel multi-arm PEG and the gel formed from the multi-arm PEG in the preparation of the materials for medical devices and the pharmaceuticals.

BACKGROUND OF THE INVENTION

Currently, the PEG derivatives are widely used for conjugation with proteins, peptides and other pharmaceuticals to extend the physical half-life of pharmaceuticals described to reduce its immunogenicity and toxicity. In clinical uses, PEG and its derivatives have been widely used in many pharmaceuticals as a carrier of pharmaceutical preparations, and the trial of bonding PEG into pharmaceutical molecules has also been under considerable development in the last decade, which is widely used in many approved pharmaceuticals, such as PEGasys®, the conjugation of α-interferon and PEG, showing a longer circulating half-life and better treatment. PEG's metabolic process in the human body has been quite clear, which is a safe synthetic polymer material without side effects.

As a safe synthetic polymer material without side effects, PEG is also widely used in the preparation of new medical devices. For example, Baxter's CoSeal, Covidien's SprayGel and DuraSeal are all new types of medical equipment listed in the U.S. or Europe in recent years. They have applied a multi-arm PEG. These products are not marketed in China.

In terms of pharmaceutical modification, compared to straight-chain PEG, the multi-arm PEG has multiple end groups, and thus has the advantage of loading multiple pharmaceutical molecules through multiple connection points with pharmaceuticals. Currently, the multi-arm PEG is widely used in PEG modification of peptide and small molecule pharmaceuticals. In application of medical devices, the multi-arm PEG can be used as crosslinking agents in production of gel, while the gel can be used in medical devices as adhesives, anti-leak agents, anti-adhesion agents and hemostatic materials.

Currently, the multi-arm PEG in the market includes three arms, four arms, six arms, eight arms and so on, of which the three-arm and four-arm PEGs are induced by polymerization of ethylene oxide with glycerol and pentaerythritol as the central molecule. Since glycerol and pentaerythritol are small molecules of single molecular weight, the three-arm and four-arm PEGs induced and produced by them are similar to straight-chain PEG in molecular weight distribution, which is reflected in quality by polydispersity of less than 1.08. The six-arm and eight-arm PEGs are basically induced by polymerization of ethylene oxide with poly glycerol as the central molecule, which is a liquid mixture, the higher polyglycerol the more difficult to get products with high purity. The synthetic multi-arm PEG with poly glycerol as the central molecular initiator basically has relatively wide molecular weight distribution, which is reflected in quality by the polydispersity index of greater than 1.08. In poly glycerol, for each additional glycerol, the multi-arm PEG has an increase of only one arm. For example, the central molecule of eight-arm PEG is six polyglycerol, which requires six glycerol molecules to get together. The purity of six polyglycerol is very difficult to exceed 85%, while the polydispersity of many eight-arm PEGs is much larger than 1.08, even greater than 1.10. The relatively wide molecular weight distribution plays a limited role in the application of eight-arm PEG in pharmaceuticals. In terms of medical devices, it also adds a quality control problem. Looking for a new central molecule to replace poly glycerol has been the subject in medical and medicinal fields of multi-arm PEG. (U.S. Pat. No. 6,858,736) describes a kind of six-arm PEG with sorbitol as the central molecular initiator. As for the demand for more than six arms, saccharidemolecules have a limitation as the central molecular initiator.

The purpose of the present invention is to overcome the lack of purity in multi-arm PEG, especially in six-arm and eight-arm PEGs in the existing technology, and provide a new type of multi-arm PEG and its preparation method, as well as the active derivatives of multi-arm PEG described, the gel formed and its conjugation with pharmaceutical molecules and applications.

In particular, the present invention provides a series of multi-arm PEG with oligomeric pentaerythritol as the central molecular initiator. Since dimeric entaerythritol can generate six-arm PEG; trimeric pentaerythritol can generate eight-arm PEG; also the purity of both dimeric and trimeric pentaerythritol can be greater than 95%, the polydispersity of multi-arm PEG generated by using them as the central molecular initiator can be reduced, and product quality can be greatly improved. Meanwhile, the invention also provides the preparation method of this new multi-arm PEG as well as its conjugation with pharmaceutical molecules and formation of gel materials. The invention also relates to application of the new multi-arm PEG described and the gel it forms in the preparation of medical devices and materials.

BRIEF SUMMARY OF THE INVENTION

The present invention provides a novel multi-arm PEG, which has the structure of general formula I:

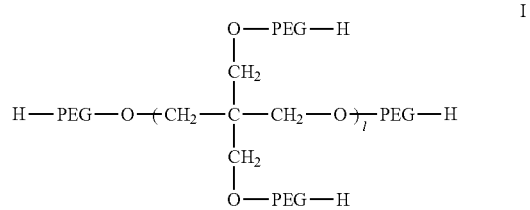

in which, the PEGs are the same or different —($CH_2CH_2O$)$_m$—, the average of m is an integer of 3-250; l is an integer ≥2.

In a preferred embodiment l is an integer ≥2 and ≤10, more preferably, an integer ≥2 and ≤5, and in particular, the optimal l is an integer ≥2 and ≤4, specifically 2 or 3.

In a preferred embodiment, the molecular weight of multi-arm PEG as described is 1000-80,000.

The invention also provides an active derivative of the novel multi-arm PEG, which has the structure of general formula II:

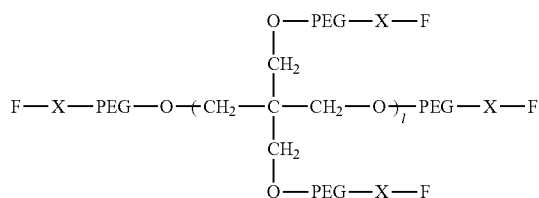

in which:

the PEGs are the same or different —(CH$_2$CH$_2$O)$_m$—, the average of m is an integer of 3-250;

l is an integer ≥2;

X is a linking group, selected from a group consisting of:

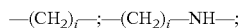

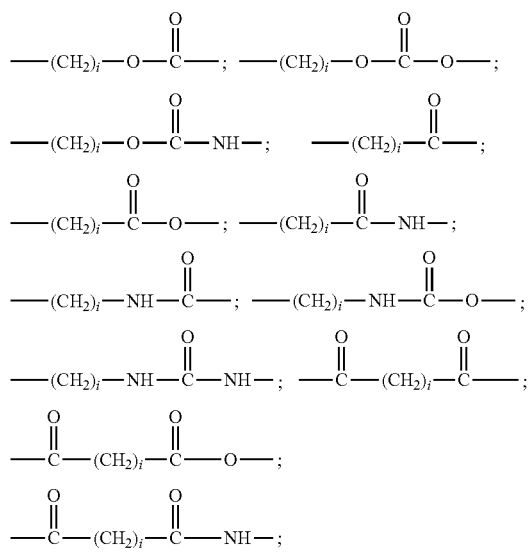

i is an integer of 0-10, preferably 0-3;

F is an active end-group, selected from a group consisting of:

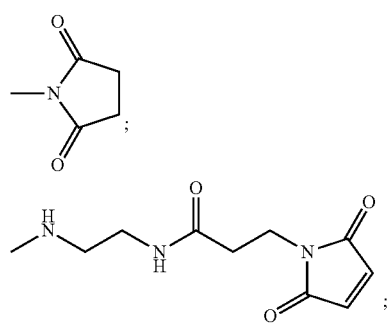

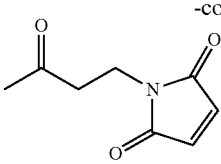

In a preferred embodiment, l is an integer ≥2 and ≤10, more preferably, an integer ≥2 and ≤5, and in particular, the optimal l is an integer ≥2 and ≤4, specifically 3.

In a preferred embodiment, the molecular weight of multi-arm PEG as described is 1000-80000.

In a specific embodiment, the active derivative of the multi-arm PEG as described is multi-arm PEG with the structure of the following general formula III:

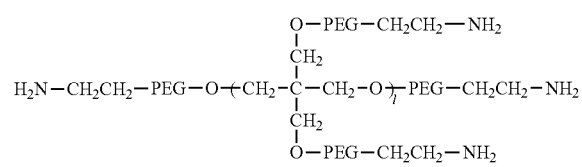

in which:

the PEGs are the same or different —(CH$_2$CH$_2$O)$_m$—, the average of m is an integer of 3-250; l is an integer ≥2, preferably 2 or 3.

In a specific embodiment, the active derivative of the multi-arm PEG as described is multi-arm PEG acetic acid with the structure of the following general formula IV:

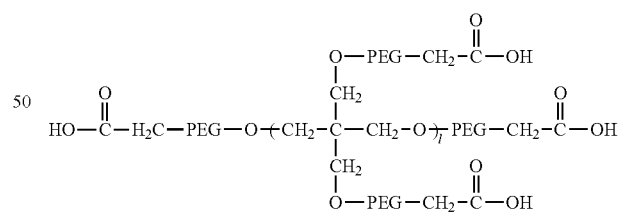

in which:

the PEGs are the same or different —(CH$_2$CH$_2$O)$_m$—, the average of m is an integer of 3-250; l is an integer ≥2, preferably 2 or 3.

In a specific embodiment, the active derivative of multi-arm PEG as described is an active NHS ester derivative of the novel multi-arm PEG with the structure of the following general formula V:

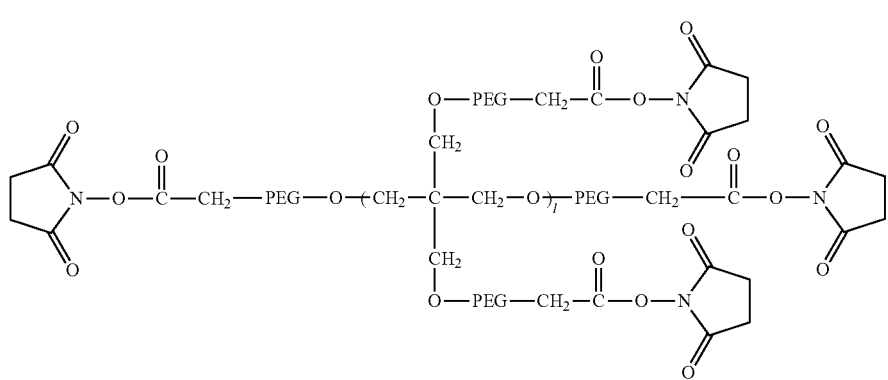

in which:

the PEG are the same or different —(CH$_2$CH$_2$O)$_m$—, the average of m is an integer of 3-250; l is an integer ≥2, preferably 2 or 3.

In a specific embodiment, the active derivative of the multi-arm PEG as described is an active MAL derivative of the new multi-arm PEG with the structure of the following general formula VI:

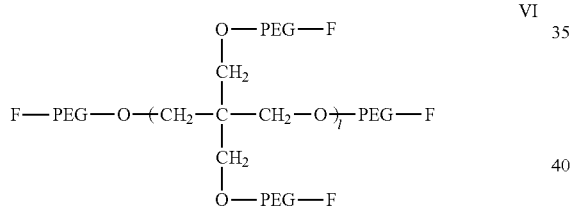

in which: F is

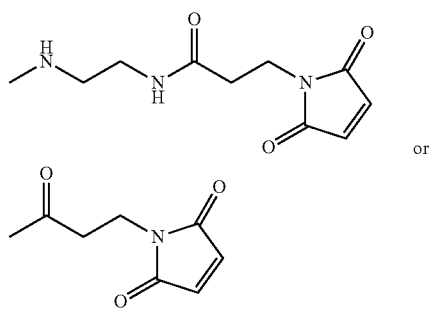

the PEGs are the same or different —(CH$_2$CH$_2$O)$_m$—, the average of m is an integer of 3-250; l is an integer ≥2, preferably 2 or 3.

In a specific embodiment, the active derivative of the multi-arm PEG as described is a succinate-active NHS ester derivatives of the new multi-arm PEG with the structure of the following general formula VII:

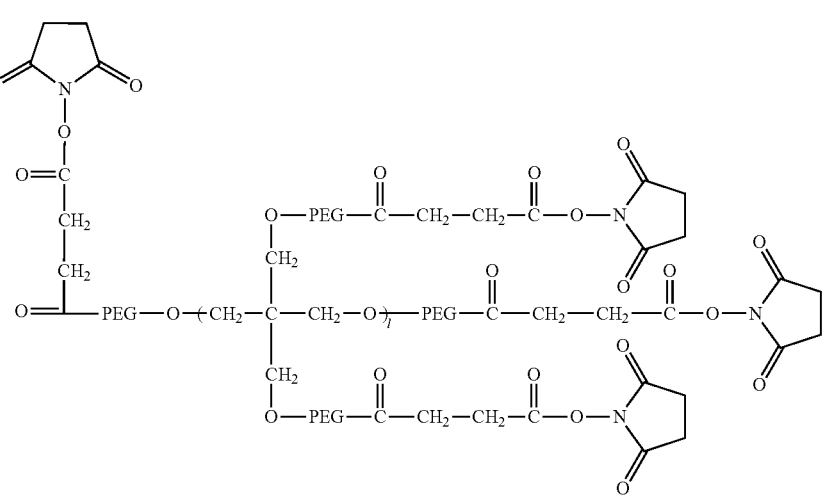

in which:
the PEGs are the same or different —(CH$_2$CH$_2$O)$_m$—, the average of m is an integer of 3-250; 1 is an integer ≥2, preferably 2 or 3.

Besides, the present invention provides a gel formed by the active derivative of the multi-arm PEG as described.

In some embodiments, the gel as described is degradable in aqueous solution. In a specific embodiment, the gel as described is formed by mixing the neutral or alkaline aqueous solution of the active derivatives of multi-arm PEG in the general formula III and VII. Preferably, the molar ratio of the active derivatives of multi-arm PEG in the general formula III and VII is 1:0.7-1:1.3.

Also the invention provides conjugation of the active derivatives of multi-arm PEG as described and pharmaceutical molecules through end group F. In some embodiments, the pharmaceutical molecules as described are selected from the group consisting of the following pharmaceutical molecules: amino acids, proteins, enzymes, nucleosides, saccharides, organic acids, flavonoids, quinones, terpenoids, phenylpropanoids, steroids and its glycosides, alkaloids and its conjugates. Preferably, the invention provides the conjugation of eight-arm PEG acetic acid and irrinitecan or docetaxel.

The invention further provides the application of these conjugates in the preparation of pharmaceuticals.

Furthermore, the invention provides the preparation methods of the new multi-arm PEG, which include the steps of ethylene oxide polymerization with pentaerythritol oligomers as an initiator.

DESCRIPTION OF THE INVENTION

Below specific examples are used to illustrate the preparation methods of the new multi-arm PEG and its active derivatives in the present invention.

The general formula of the multi-arm PEG chain structure is as follows:

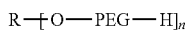

in which:
R is the non-hydroxy part of the central or initiative molecule, usually C1-12 alkyl, cycloalkyl or aralkyl;
n is the number of branches or arms;
PEG is the same or different —(CH2CH2O)m-, m is any integer, representing the degree of polymerization of PEG arm.

When R is the non-hydroxy part of pentaerythritol, the initiative molecule is pentaerythritol, whose chemical structure is as the following formula:

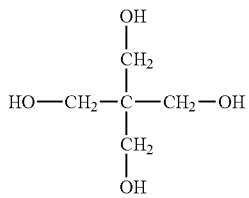

where n is equal to 4, a four-arm PEG is formed; when R is the non-hydroxy part of dimeric pentaerythritol, the initiative molecule is dimeric pentaerythritol, whose chemical structure is as follows:

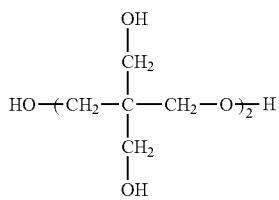

where n is equal to 6, a six-arm PEG is formed; when R is the non-hydroxy part of trimeric pentaerythritol, the initiative molecule is trimeric pentaerythritol, whose chemical structure is as follows:

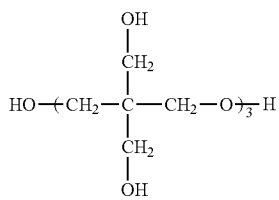

where n is equal to 8, an eight-arm PEG is formed.

In terms of PEG, molecular weight is commonly used, as long as the molecular weight of single arm of the PEG formed is 300 to 60,000 Dalton, which means m is about 6 to 1300. More preferably, m is 28, 112 or 450, which corresponds to molecular weight of 1325, 5000 or 20,000. Due to the potential heterogeneity of the starting PEG compound limited by its average molecular weight rather than self-repeated unit, molecular weight is preferred to characterize PEG polymers, rather than using m to represent the self-repeated unit in PEG polymers.

According to the invention, PEG can be prepared through polymerization with oligomeric pentaerythritol as an initiator; the preparation process as described can be available in accordance with the general synthesis and preparation methods in the field. Different claim-based structures of compound require adopting appropriate synthesis and preparation methods; specific circumstances can refer to various technologic literature and patent outcomes in the field.

Active Groups:

In the application of the active derivatives of multi-arm PEG according to the present invention, different functional end group F determines the different purposes of derivatives. The introduction of these functional groups will determine the applied field and structure of derivatives. The most common functional group is NHS, as the formula V shows. The active derivatives of NHS ester structure can be linked with groups of amine structure.

Similarly, according to the description of this manual, the technicians in this field can obtain the active derivatives of multi-arm PEG with amine functional groups, as the formula III shows.

Similarly, the technicians in this field can obtain the active derivatives of multi-arm PEG with carboxyl functional groups, as the formula IV shows.

Similarly, the technicians in this field can obtain the active derivatives of multi-arm PEG with maleimide functional groups (MAL), as the formula VI shows. The active derivatives of MAL structure can be linked with groups of thiol structure.

Many pharmaceuticals contain active amino, carboxyl, hydroxyl and other functional groups, which usually conjugate with simple saccharides, polysaccharides, nucleosides, poly nucleosides, phosphorus acyl and other elements to form active pharmacological structure in organisms.

Therefore, PEG derivatives modified by functional groups can conjugate with these pharmaceutical molecules in the same way as an alternative to bio-organic molecules, so as to overcome the disadvantages of short physical half-life and short efficacy duration of bio-organic molecules in organisms.

The active derivatives of multi-arm PEG in the present invention can conjugate with pharmaceutical molecules through appropriate functional groups (F), which link proteins, peptides or other free amino, hydroxyl, sulfur, hydroxyl, etc. in natural medicines with PEG derivatives. For small molecular pharmaceuticals, each multi-arm PEG molecule can bond multiple pharmaceutical molecules. Such PEG derivatives have a higher pharmaceutical loading rate to ensure proper pharmaceutical concentration and enhanced release features so as to improve the physiological function of pharmaceutical molecules in organisms.

All of the above applications are intended to provide a possible reference model for the medical application of PEG derivatives; the specific use and selection must be confirmed according to pharmacological, toxicological, clinical and other necessary experiments.

In the conjugates of the present invention, pharmaceutical molecules are preferably amino acids, proteins, enzymes, nucleotides, carbohydrates, organic acids, flavonoids, quinones, terpenoids, phenylpropanoid phenols, steroids, glycosides, biological alkali, etc. While pharmaceutical molecules in protein are preferably interferon drugs, EPO drugs, growth hormone drugs, antibody drugs, and so on.

The conjugates of the present invention can be delivered in the form of pure compounds or suitable pharmaceutical composition, through any acceptable mode of delivery or reagents used for similar purposes. Therefore, the delivery mode through mouth, nasal, rectal, transdermal or injection can be adopted, in the form of solid, semi-solid, lyophilized powder or liquid reagents, for example, tablets, suppositories, pills, soft and hard gelatin capsules, powder, solution, agents, suspensions or aerosols, etc., preferably the unit form of simple delivery for precise dosage. Composition may contain conventional pharmaceutical carrier or excipient and the conjugates of the present invention as the active ingredient (one or more); in addition, it can also contain other agents, carriers, auxiliary agents, etc.

Typically, depending on the desired mode of delivery, a pharmaceutically acceptable composition will contain about 1-99 weight % of the conjugates of the invention, and 99-1 weight % of the appropriate medicinal excipients. Preferred composition contains about 5-75 weight % of the conjugates of the invention, and appropriate pharmaceutical excipients for the rest.

The preferred way of delivery is injection, through conventional daily dose program, which can be adjusted according to the severity of disease. The conjugates of the present invention or a pharmaceutically acceptable salt can be formulated into injectable agent; for example, dispersing about 0.5-50% of the active ingredient in medicinal adjuvant which can be delivered in liquid form, such as water, salt water, glucose water, glycerol, ethanol, etc., to form the solution or suspension agent.

The pharmaceutical compositions can be delivered in liquid form; for example, dissolving and dispersing the conjugates of the present invention (about 0.5-20%) and selected existing pharmaceutical auxiliary agent in the carrier, such as water, salt water, glucose water, glycerol, ethanol, etc., to form the solution or suspension agent.

If necessary, the pharmaceutical compositions of the invention can also contain small amounts of auxiliary substances, such as wetting agents or emulsifiers, pH buffers, antioxidants, etc., for example: citric acid, dehydrated sorbitol monolaurate, triethanolamine oil ester, butylated hydroxy toluene.

The actual preparation of such formulations is known or obvious to technical staff in the field, which can be found in *Remington's Pharmaceutical Sciences,* 18th Edition, (Mack Publishing Company, Easton, Pa., 1990). In any case, in accordance with the technology of the invention, the compositions used will contain therapeutically effective amount of conjugates of the invention for the treatment of appropriate disease.

EXAMPLES

Below is description with examples of the conjugates of the invention and its preparation method, which does not limit the present invention; the scope of the present invention is limited by the claims.

Unless otherwise indicated, the reagents used in the following Examples are purchased from Beijing Chemical Reagent Company or other similar companies selling public chemicals.

Example 1

Synthesis of Six-Arm PEG 10000

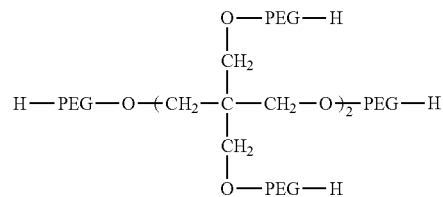

Put dimeric pentaerythritol (2540 g) and appropriate amount of catalyst into the reactor together. Heat it until 110° C. Vacuum for 2 hours. Introduce 100 kg of ethylene oxide until the reaction is completed. Products are measured by MALDI to determine molecular weight, which is 10000. NMR (DMSO) δ: 3.50 (br, m, hydrogen in PEG), 4.58 (t, 6×1 hydrogen).

Example 2

Synthesis of eight-arm PEG 10000

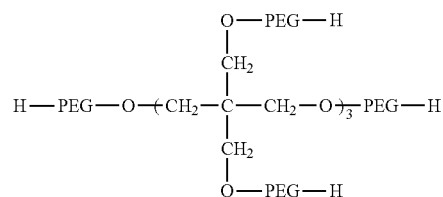

Put trimeric pentaerythritol (3720 g) and appropriate amount of catalyst into the reactor together. Heat it until 110° C. Vacuum for 2 hours. Introduce 100 kg of ethylene oxide until the reaction is completed. Products are measured by MALDI to determine molecular weight, which is 10000. NMR (DMSO) δ: 3.50 (br, m, hydrogen in PEG), 4.58 (t, 6×1 hydrogen).

Example 3

Synthesis of eight-arm PEG amine (IIIa)

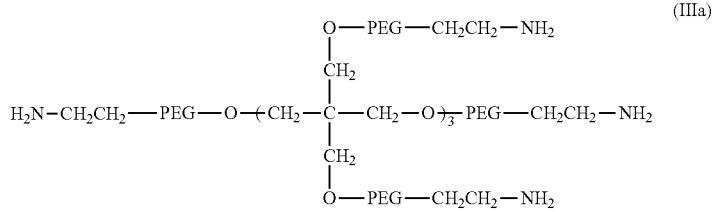

Put 100 grams of eight-arm PEG with the molecular weight of 10,000 (obtained in Example 2) in nitrogen atmosphere for azeotropic distillation with toluene for 2 hours, and then reduce to room temperature. Add 300 ml of dry dichloromethane and 28 ml of triethylamine. Cool the mixture in an ice bath and add dry chloride drop by drop, stir in nitrogen atmosphere at room temperature overnight, and then add 30 ml of ethanol to stop the reaction immediately. Recycle the solvent with rotary evaporator for concentration, filter out the sediment, and then add 500 ml of ether, filter and collect sediment to dry in vacuum. Yield: 95 g (95%).

Dissolve 50 grams of eight-arm PEG-methyl sulfonyl ester with the molecular weight of 10,000 (obtained in last step) into 3000 ml of ammonia solution with 5% of ammonium chloride. Stir the solution at room temperature for 72 hours, extract it with dichloromethane solution for three times, then combine organic phase and dry with anhydrous sodium sulfate. Distill the solvent in vacuum, add the residue into 500 ml of isopropanol, and collect sediment to dry in vacuum. Yield: 0.7 g (70%). NMR (DMSO) δ: 3.50 (br, m, hydrogen in PEG), 2.61 (t, 8×2 hydrogen).

Example 4

Synthesis of eight-arm PEG acetic acid (IVa)

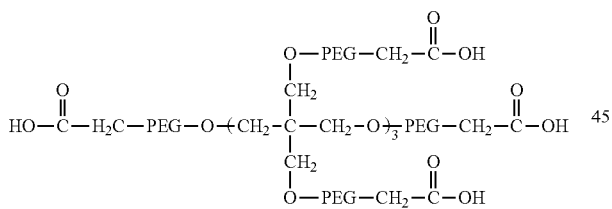

Put 40 grams of eight-arm PEG with the molecular weight of 10,000 (obtained in Example 2) into a 1000 ml flask, add 500 ml of toluene, and evaporate out 150 ml of toluene through heating in a nitrogen atmosphere. After cooling the solution down till 50° C., add 30 ml of toluene solution with 16 g of potassium tert-butylate for isothermal reaction for 2 hours, then reduce to room temperature, add 16 ml of tert-Butyl bromoacetate, stir in nitrogen atmosphere overnight. Evaporated, add into 1 liter of isopropanol for sedimentation; filter the sediment for washing, and then vacuum drying.

Prepare 2 liters of NaOH solution with pH=12, and add the above product for hydrolysis overnight. Adjust concentrated hydrochloric acid to pH=2, add 100 g of sodium chloride to dissolve, extract with dichloromethane for 3 times, and combine extracts; then dry with anhydrous sodium sulfate, evaporate the organic phase, add to 1 liter of isopropanol for sedimentation, filter the sediment for washing, and then vacuum drying. Thus eight-arm PEG acetic acid is obtained (IV), yield: 32 g (80%), NMR (DMSO) δ: 3.50 (br, m, hydrogen in PEG), 2.61 (t, 8×2 hydrogen).

Example 5

Synthesis of Eight-Arm PEG Acetic Acid-NHS Ester with the Activity to Amino Group (Va)

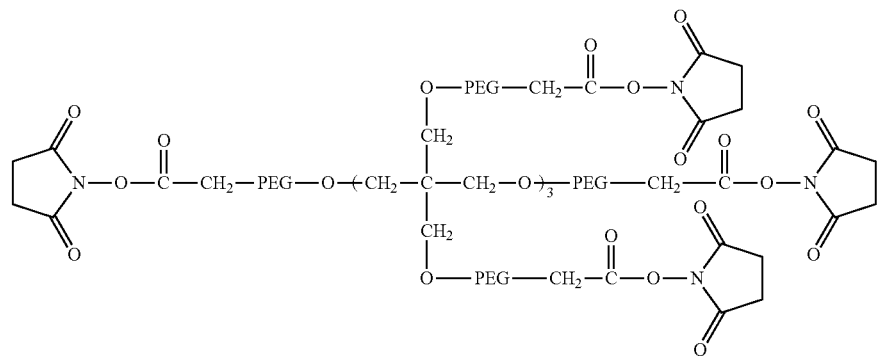

Dissolve 10 grams of eight-arm PEG acetic acid (with molecular weight of 10,000, obtained in Example 4) in 100 ml of dichloromethane, add 900 mg of N-hydroxysuccinimide and 2.5 g of dicyclohexyl carbodiimide, stir at room temperature for 6 hours, and distill the solvent in vacuum. Put the residue into 500 ml of isopropanol, filter and collect sediment for drying in vacuum. Yield: 9.6 g (96%). NMR (DMSO) δ: 3.50 (br, m, hydrogen in PEG), 2.81 (s, 8×4 hydrogen), 4.58 (s, 8×2 hydrogen).

Example 6

Synthesis of Eight-Arm PEG Maleimide with the Activity to S-Hydroxy Group (VIa)

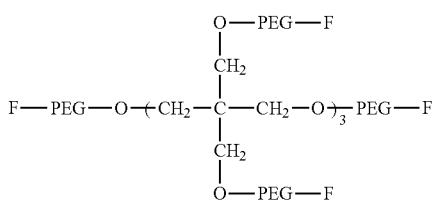

VIa in which: F is

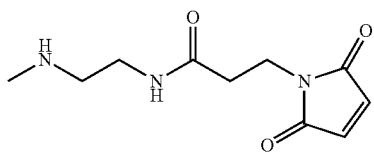 [SMILES: CNCCNC(=O)CCN1C(=O)C=CC1=O]

Dissolve 5 grams of eight-arm PEG amine with the molecular weight of 10,000 (obtained in Example 3) in acetonitrile, add to the solution 30 mg of maleimide acid-N-succinimide ester, stir the solution at room temperature overnight, and distill the solvent in vacuum; add the residue into 100 ml of isopropanol, then collect the sediment and dry in vacuum. Yield: 4.2 g (84%). NMR (DMSO) δ: 3.50 (br, m, hydrogen in PEG), 2.56 (t, 8×2 hydrogen), 6.71 (s, 8×2 hydrogen in maleimide).

Example 7

Synthesis of Eight-Arm PEG Succinate-NHS Ester with the Activity to Amino Group (VII a)

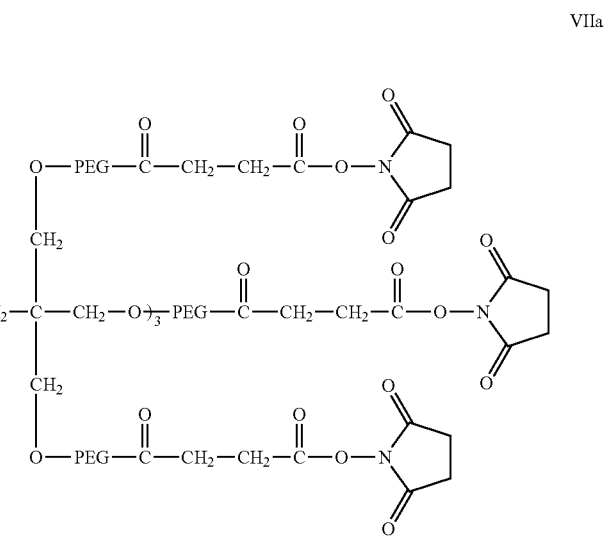

VIIa

Add 100 grams of eight-arm PEG with the molecular weight of 10,000 (obtained in Example 2) to 1000 ml of toluene, evaporate out 250 ml of toluene through heating in nitrogen atmosphere; after the solution is cooled down to 50° C., add 16 grams of succinate anhydride to reflux for 6 hours, then reduce to room temperature, add 16 grams of tert-Butyl bromoacetate, and stir under the protection of N2 overnight. Evaporated, add to 1 liter of isopropanol for sedimentation, and then filter the sediment, wash and dry in vacuum.

Further dissolve the above product in 500 ml of methylene chloride, add 10 grams of N-hydroxysuccinimide and 25 grams of dicyclohexyl carbodiimide, and stir at room temperature for 6 hours before vacuum recycling the solvent, then add the residue to 500 ml of isopropanol, filter and collect sediment and dry in vacuum. Yield: 92 g (92%).

NMR (DMSO) δ: 3.50 (br, m, hydrogen in PEG), 2.81 (s, 8×4 hydrogen), 4.28 (t, 8×2 hydrogen), 2.58 (t, 8×2 hydrogen), 2.93 (t, 8×2 hydrogen).

Example 8

Synthesis of Biodegradable Eight-Arm PEG Gel

Dissolve 1 gram of eight-arm PEG amine (IIIa) with the molecular weight of 10,000 (obtained in Example 3) in 10 ml of phosphate buffer (100 mM, pH 9). Dissolve 1 gram of eight-arm PEG succinate-NHS ester with the molecular weight of 10,000 (VIIa) (obtained in Example 7) in 10 ml of phosphate salt buffer (pH 7.4). Then mix these two solutions quickly, put it aside so that biodegradable eight-arm PEG gel will be formed within 1 minute. Put the gel formed into 100 ml of phosphate salt buffer (pH 7.4) and store it at 37° C., the gel will degrade and dissolve within 10 days.

Example 9

Synthesis of Stable Eight-Arm PEG Gel

Dissolve 1 gram of eight-arm PEG amine (IIIa) with the molecular weight of 10,000 (obtained in Example 3) in 10 ml of phosphate buffer (100 mM, pH 9). Dissolve 1 gram of eight-arm PEG acetic acid-NHS ester (Va) (obtained in Example 5) in 10 ml of phosphate salt buffer (pH 7.4). Then mix these two solutions quickly, put it aside so that eight-arm PEG gel will be formed within 1 minute. Put the gel formed into 100 ml of phosphate salt buffer (pH 7.4) and store it at 37° C., the gel will remain stable within 360 days without degrading or dissolving.

Example 10

Conjugate of Eight-Arm PEG Acetic Acid and Docetaxel

Dissolve 1 gram of eight-arm PEG acetic acid (IVa) (obtained in Example 4) in 10 ml of dichloromethane, then add 90 mg of docetaxel (purchased from Chengdu Furunde Industrial Co., Ltd.), 8 mg of dimethylamino pyridine and 25 mg of dicyclohexyl carbodiimide. Stir this solution at room temperature for 6 hours before vacuum recycling the solvent, add the residue into 20 ml of isopropanol, filter and collect sediment and then wash with ethyl ether before vacuum drying. Yield: 0.8 g (80%), melting point: 55-57° C.

Example 11

Conjugate of Eight-Arm PEG Acetic Acid and Irrinitecan Derivatives

Dissolve 1 gram of eight-arm PEG acetic acid (IVa) (obtained in Example 4) in 10 ml of dichloromethane, and then add 0.12 g of glycine-irrinitecan (purchased from Chengdu Furunde Industry Co., Ltd.), 50 mg of dimethylamino pyridine and 95 mg of dicyclohexyl carbodiimide. Stir this solution at room temperature for 6 hours before vacuum recycling the solvent, then add the residue into 20 ml of 1,4-dioxane to dissolve. Filter to remove sediment, evaporate the solution, add the residue into 20 ml of diethyl ether, and filter to collect sediment before washing with diethyl ether and vacuum drying. Yield: 0.8 g (80%), melting point: 56-58° C.

Example 12

Conjugate of Eight-Arm PEG Acetic Acid and Scopoletin

Dissolve 1 gram of eight-arm PEG acetic acid (IVa) (obtained in Example 4) in 20 ml of dichloromethane, then add 30 mg of scopoletin (purchased from Tianjin Cenway Company), 20 mg of 1-hydroxy benzotriazole, 20 mg of dimethylamino pyridine and 38 mg of dicyclohexyl carbodiimide. Stir this solution at room temperature for 12 hours under nitrogen before vacuum recycling the solvent, add the residue into 20 ml of 1,4-dioxane, filter to collect sediment before washing with diethyl ether and drying. After vacuum recovery of solvent, add the residue into 100 ml of isopropanol, filter to collect sediment before washing with diethyl ether and drying. Combine the sediments for vacuum drying. Yield: 0.92 g (92%), melting point: 56-58° C.

Example 13

Preparation of Pharmaceutical Composition

This Example illustrates the preparation process of typical pharmaceutical composition with non-gastrointestinal delivery, which contains conjugates of the present invention.

Components

Conjugate in Example 11 2 g 0.9% of saline solution Up to 100 ml

Dissolve 2 grams of the conjugation in Example 11 into 0.9% of saline solution to obtain 100 ml of intravenous solution, before filtering with 0.2 μm membrane material and packaging under sterile conditions.

The invention claimed is:

1. An active derivative of a multi-arm polyethylene glycol of the general formula II for conjugating with a pharmaceutical molecule, and wherein the derivative has a polydispersity of less than 1.08:

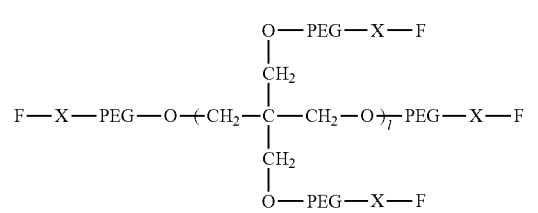

II in which, the PEGS are the same or different —(CH$_2$CH$_2$O )$_m$—, the average of m is an integer of 28-112;

l is an integer of 3 or 4;

X is a linking group, selected from a group consisting of the following groups:

—(CH$_2$)$_i$— ; —(CH$_2$)$_i$—NH— ;

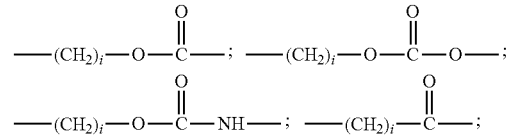

-continued

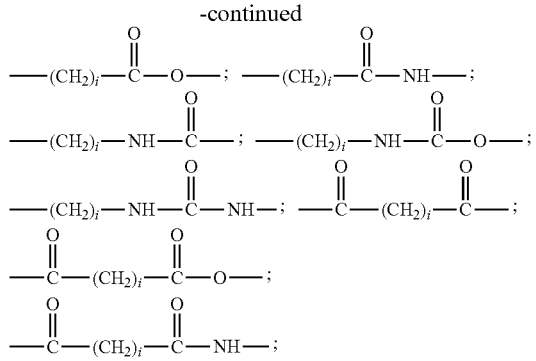

i is an integer of 0-10;
each F is identically the same active end-group, selected from a group consisting of:

—H; —NH₂;

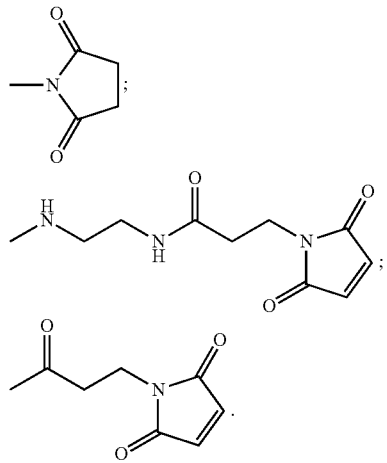

2. The active derivative of the multi-arm polyethylene glycol of claim 1, wherein the molecular weight of multi-arm polyethylene glycol is less than 40,000 daltons.

3. The active derivative of the multi-arm polyethylene glycol of claim 1, having a structure of the following general formula III:

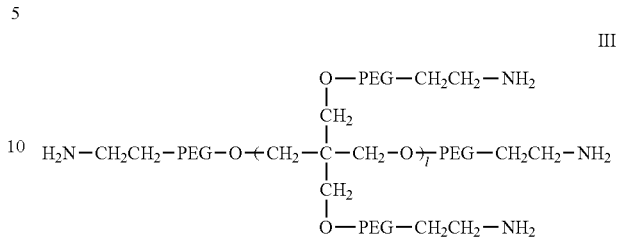

in which:
the PEGS are the same or different —$(CH_2CH_2O)_m$—, the average of m is an integer of 28-112; and
l is an integer of 3 or 4.

4. The active derivative of the multi-arm polyethylene glycol of claim 1, having a structure of the following general formula IV:

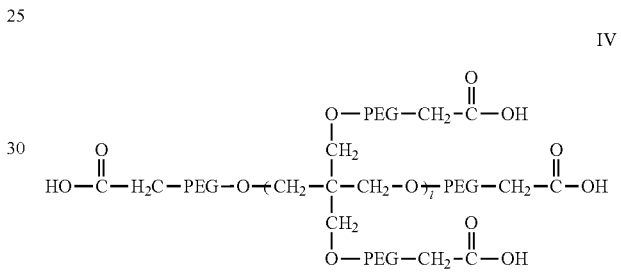

in which:
the PEGS are the same or different —$(CH_2CH_2O)_m$—, the average of m is an integer of 28-112; and
l is an integer of 3 or 4.

5. The active derivative of the multi-arm polyethylene glycol of claim 1, having a structure of the following general formula V:

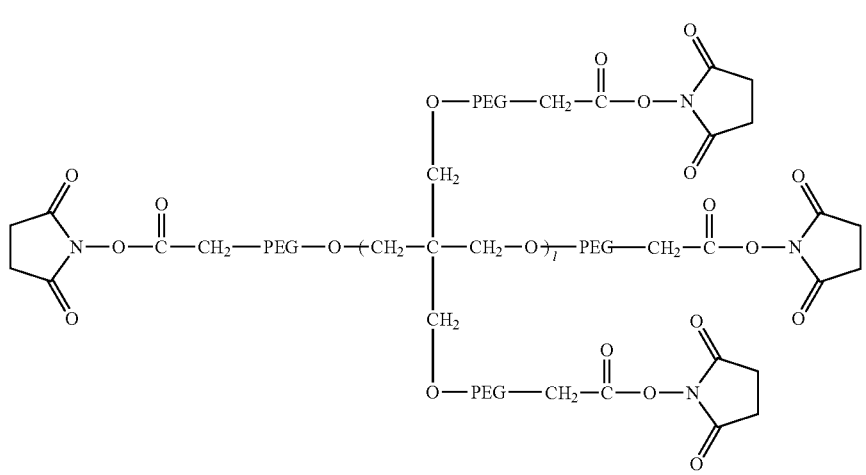

in which:

the PEGs are the same or different —(CH$_2$CH$_2$O)$_m$—, the average of m is an integer of 28-112; and l is an integer of 3 or 4.

6. The active derivative of the multi-arm polyethylene glycol of claim 1, having a structure of the following general formula VI:

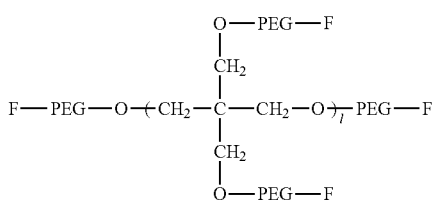

VI in which: F is

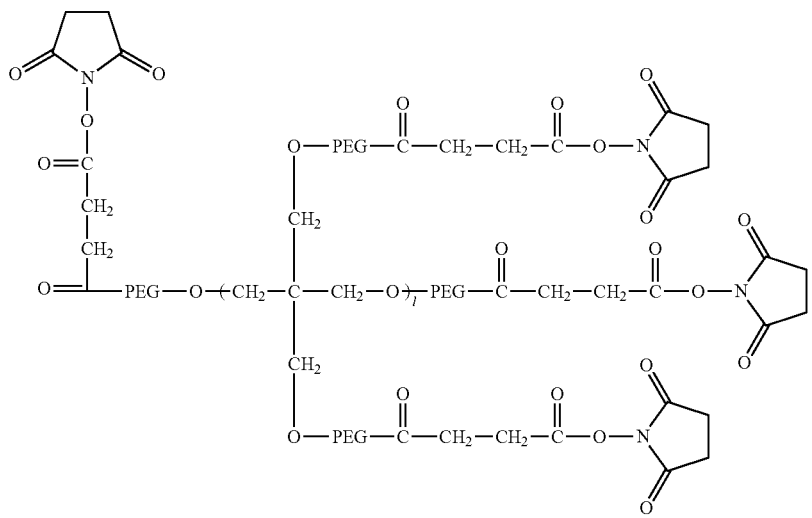

the PEGS are the same or different —(CH$_2$CH$_2$O)$_m$—, the average of m is an integer of 28-112;

l is an integer of 3 or 4.

7. The active derivative of multi-arm polyethylene glycol of claim 1, having a structure of the following general formula VII:

VII in which:

the PEGS are the same or different —(CH$_2$CH$_2$O)$_m$—, the average of m is an integer of 28-112; and l is an integer of 3 or 4.

8. The active derivative of the multi-arm polyethylene glycol of claim 3, wherein l is 3.

* * * * *